United States Patent [19]
Patat et al.

[11] Patent Number: 5,618,549
[45] Date of Patent: Apr. 8, 1997

[54] USE OF PARTICLES OF A BIOCOMPATIBLE AND BIOABSORBABLE CALCIUM SALT AS ACTIVE INGREDIENT IN THE PREPARATION OF A MEDICINAL PRODUCT INTENDED FOR THE LOCAL TREATMENT OF BONE DEMINERALIZATION DISEASES

[75] Inventors: Jean-Louis Patat; Yves Cirotteau, both of Paris, France

[73] Assignee: Inoteb, Saint Gonnery, France

[21] Appl. No.: 360,823

[22] PCT Filed: May 11, 1994

[86] PCT No.: PCT/FR94/00564

§ 371 Date: Feb. 2, 1995

§ 102(e) Date: Feb. 2, 1995

[87] PCT Pub. No.: WO94/26283

PCT Pub. Date: Nov. 24, 1994

[30] Foreign Application Priority Data

May 13, 1993 [FR] France .................................. 93 05783

[51] Int. Cl.⁶ ...................................................... A61F 2/28
[52] U.S. Cl. ........................... 424/422; 424/423; 424/602
[58] Field of Search ..................... 424/422, 602, 424/423

[56] References Cited

U.S. PATENT DOCUMENTS

| | | | |
|---|---|---|---|
| 4,440,750 | 4/1984 | Glowacki et al. | 424/177 |
| 4,743,229 | 5/1988 | Chu | 604/82 |
| 4,770,860 | 9/1988 | Ewers et al. | |
| 4,789,663 | 12/1988 | Wallace et al. | 424/423 |
| 4,917,702 | 4/1990 | Scheicher et al. | |
| 5,085,861 | 2/1992 | Gerhart et al. | 424/78.17 |
| 5,125,971 | 6/1992 | Nonami et al. | 106/35 |
| 5,158,934 | 10/1992 | Ammann et al. | 514/12 |

FOREIGN PATENT DOCUMENTS

| | | |
|---|---|---|
| 0395187 | 10/1990 | European Pat. Off. . |
| 2448900 | 9/1980 | France . |
| 2460657 | 1/1981 | France . |
| 2637502 | 4/1990 | France . |
| 4130546 | 3/1993 | Germany . |
| 86/01726 | 3/1986 | WIPO . |
| 87/03491 | 6/1987 | WIPO . |
| 89/06944 | 8/1989 | WIPO . |

*Primary Examiner*—Paul R. Michl
*Assistant Examiner*—Sharon Howard
*Attorney, Agent, or Firm*—Oliff & Berridge

[57] ABSTRACT

A method of treating a living organism having a disease associated with demineralization or mineralization defects of an existing bone by applying in a spongy portion of the bone or in a medullary canal of the bone at least one biocompatible and bioabsorbable calcium salt in the form of particles having dimensions less than 8 mm. The biocompatible and bioabsorbable calcium salt is an active ingredient for reinitiating bone remineralization and reconstruction of resorbed bone spans and increases bone density and bone mass.

16 Claims, No Drawings

USE OF PARTICLES OF A BIOCOMPATIBLE AND BIOABSORBABLE CALCIUM SALT AS ACTIVE INGREDIENT IN THE PREPARATION OF A MEDICINAL PRODUCT INTENDED FOR THE LOCAL TREATMENT OF BONE DEMINERALIZATION DISEASES

FIELD OF THE INVENTION

The invention relates to the field of treatment of certain bone diseases.

It is known that bone is a continuously regenerated tissue. Schematically, osteoblasts secrete an inorganic matrix consisting mainly of hydroxyapatite and the osteoblast surrounded by this inorganic matrix converts into an osteocyte. In parallel, specialized cells, such as osteoclasts break down the inorganic matrix. In healthy bone, the space thus liberated is reoccupied by osteoblasts and so on.

It is important to retain a balance between osteogenesis and osseous resorption so that the bone can fulfil its function in the skeleton.

BACKGROUND

A number of diseases are known which are associated with demineralization or mineralization disorders of bone. The most well-known disease is without doubt osteoporosis, in which the regeneration of the bone tissue is imbalanced because the breakdown of the bone matrix by the osteoclasts becomes predominant. The activity of the osteoblasts is greatly decreased and, as the disease progresses, the inorganic matrix is present in an insufficient quantity to allow activity of the osteoblasts to develop normally. The result of this is that the reconstruction of the bone matrix is interrupted or, in any case, insufficient to maintain the conditions necessary for the osteogenesis process. The number, thickness and relative volume of the bone-tissue bridges in the spongy bone are reduced. The density of the bone decreases, which leads to greater mechanical fragility. This results in bone fractures due to impact or falling (especially fractures of the femur, of the wrists or of the humerus) or else vertebral compressions under the pressure exerted by the weight of the body. Repairing such fractures may become difficult because of the small mass of bone available for repair. It is known, in particular, that fractures of the neck of the femur in the elderly suffering from osteoporosis can lead to death in approximately 20% of cases.

Other diseases are accompanied by demineralization or weak mineralization or a mineralization defect of the bone. This is the case, in particular, of Paget's disease, fibrous dysplasias and osteodystrophies caused, in particular, by certain renal insufficiencies. In addition, demineralization of the jaw bone may be the cause of certain periodontal diseases.

Until now, the treatments of demineralization diseases of the bone, in particular osteoporosis, comprise oral supply of calcium, optionally in association with vitamin D, or the administration of oestrogens, optionally in combination with progestogens. These treatments can arrest the breakdown process, but without allowing remineralization by regeneration of the interstitial bone tissue.

The administration of fluorides, also orally, stimulates the osteoblast activity and can lead to an increase in the bone mass by 5 to 10% per year in responsive patients (approximately 60% of cases). However, treatment using fluorides has the drawback of some degree of cumulative toxicity, with the appearance of bone microfractures which can cause significant amounts of pain.

SUMMARY OF THE INVENTION

It has now been discovered that it is possible to reinitiate remineralization of the bone by locally supplying calcium in the form of a biocompatible and bioabsorbable salt.

It has been observed that the local application, within the bone, of a calcium salt makes it possible to reinitiate a process of remineralization and regeneration of the interstitial bone tissue with, in particular, increase of the bone density (and therefore the solidity of the bone), whereas oral supply of calcium does not make it possible to reinitiate the process of reconstruction of the resorbed bone spans. In addition, by virtue of this local treatment, remineralization is particularly rapid. It should be noted that the remineralization process extends throughout the bone and is not limited to the part which is in contact with the region where the calcium salt is implanted.

The use has already been described of various calcium salts, and in particular carbonate (especially in the form of coral) or phosphates (especially in the form of hydroxyapatite) as implants which can be used as bone prosthesis parts or as fillers promoting reincorporation by the newly formed bone, especially in the case where the prosthetic material is biodegradable or includes an open pore system.

DESCRIPTION OF PREFERRED EMBODIMENTS

The subject of the invention is therefore the use of at least one biocompatible and bioabsorbable calcium salt, in the form of particles having dimensions less than 8 mm, as active ingredient in the preparation of a medicinal product intended for local treatment of diseases associated with demineralization or mineralization defects of bone, especially with the aim of re-establishing the bone remineralization process.

The medicinal product obtained according to the invention can be used, in particular, in the treatment of osteoporosis, Paget's disease, fibrous dysplasias and osteodystrophies. It should, in particular, be noted that, in the case of osteoporosis, when significant fragility of the bones, and especially of the femur, has been detected, it is possible to treat the patient before a fracture occurs.

Among the calcium salts which can be used, mention will, in particular, be made of gluconate, tartrate, glycerophosphate, sulphate, carbonate and phosphates, including fluorophosphate, tricalcium phosphate, etc.

These various calcium salts have different absorption times, depending in particular on their solubility. It is thus possible to alter the absorption rate by mixing calcium salts which have different absorption rates, which makes it possible both to supply calcium rapidly and to provide a reserve for long-term supply.

When they are present, the phosphates such as tricalcium phosphate or hydroxyapatite, which are weakly absorbed, are preferably employed mixed with other calcium salts which are absorbed more rapidly. According to one particular embodiment, use is made of an active ingredient which is free of phosphates.

The material forming the active ingredient may be present, in particular, in the form of small balls, cylinders or granulates. These particles are prepared according to the normal methods.

They generally have dimensions of less than 5 mm. Most often, use will be made of particles having dimensions of from 0.2 to 4 mm, and especially from 0.3 to 3 mm. The absorption rate increases when the dimensions of the particles decrease.

In a particular embodiment, the active ingredient of the medicinal product obtained according to the invention contains at least one calcium carbonate in the form of aragonite or calcite. The carbonate may be a naturally occurring material obtained, in particular, from madreporal coral skeletons (in particular Porites, Pocillopora, Acropora or Favites) or mollusc shells (for example *Pinctada margaritifera*). Among the natural calcite-based materials, mention will, in particular, Be made of materials obtained from echinoderm skeleton, especially spines of a sea urchin (such as Citaris). The treatments which are carried out, for example, on the raw coral material in order to convert it into a biocompatible material (washings, sterilizations.) are described, in particular, in document FR-2,460,657.

The balls, cylinders or granulates can be obtained, in particular, by grinding, by machining and/or by wear. They may consist of a porous or non-porous material.

The medicinal product obtained according to the invention may consist of a powder which can be administered by injection (especially in the case of small balls), using an injector device fitted with a trocar. In the case of an open operation, for example when fitting osteosynthesis parts after a fracture of the neck of the femur, the medicinal product according to the invention can be applied directly. In some cases, application within the bone will be facilitated by mixing the calcium salt with a vehicle allowing the medicinal product to be given the consistency of a fluid paste. The vehicle making it possible to present the medicinal product in the form of a fluid paste may be physiological saline solution or else blood, blood plasma, bone marrow or a biological adhesive. These naturally occurring vehicles may be autologous products, that is to say sampled from the actual individual who is being treated or obtained from substances sampled from the individual being treated.

It is also possible to mix the calcium salt particles or impregnate them with at least one substance which promotes osteogenesis, for example strontium salts (especially carbonate), fluorides (for example sodium fluoride), growth factors, etc.

Blood and bone marrow, in particular, contain such growth factors.

The medicinal product obtained according to the invention can also be prepared in the form of a fluid paste using a solution or suspension of proteins such as, for example, collagen, fibronectin, etc., or using a biocompatible gelling agent such as carboxymethylcellulose or methylcellulose.

In the medicinal product obtained according to the invention, the calcium salt generally represents from 40 to 100% by weight with respect to the total weight of the medicinal product, and in particular from 40 to 97%.

The medicinal compound obtained according to the invention is administered into the spongy bone and/or into the medullary canal, so as to apply an effective quantity of the calcium salt, which depends on the calcium salt used and the bone to be treated (especially the volume of bone) and on the condition of the patient. Generally, from 1 to 25 g of calcium is administered using the medicinal product obtained according to the invention. In the case of treating a femur or a humerus, the medicinal product obtained according to the invention is administered so as to implant, for example, from 2 to 20 g of calcium. In a vertebra, it is possible, for example, to administer a quantity of medicinal product which is sufficient to supply from 2 to 15 g of calcium.

In a preferred embodiment, the medicinal product of the invention contains growth factors.

It is known that growth factors are substances which promote, in particular, the regeneration of cells and tissues, and some of which have been recommended, in particular, in the treatment of osteoporosis. In the case of an in vivo cellular lesion, the thrombocytes (or platelets) release numerous growth factors, such as, for example, PDGF (platelet-derived growth factor), TGF-β (transforming growth factor β), IGF-I and IGF-II (insulin-related growth factor), etc.

It will be recalled that the term "biological adhesives" is used to denote concentrates of proteins which can be coagulated by thrombin, or solutions of fibrinogen which are used in the production of an adhesive material which makes it possible, in particular, to connect living tissues while exerting a haemostatic action; see, for example Patent FR-2,448,900. It is possible to prepare biological adhesives enriched in platelet-derived growth factors, for example according to the method of Patent Application FR no. 92.11643, filed by the Applicant Company on 30 Sep. 1992, this method principally consisting in freezing a platelet-enriched plasma and in collecting a cryoprecipitate, constituting the said adhesive, by heating the frozen plasma to a temperature of approximately +1 to +6° C., and in particular in the region of +4° C.

The following examples illustrate the invention.

EXAMPLE 1

Use is made of a first medicinal product consisting of Porites coral balls having dimensions of 2 to 3 mm, marketed under the name BIO-SPHERE by the Company INOTEB.

Use was also made of a second medicinal product consisting of Acropora coral granulates having dimensions of 0.3 to 1 mm, mixed with collagen gel, in the form of a paste marketed under the name BIOCORAL GEL by the Company INOTEB. This product contains 65% by weight of coral granulates.

These medicinal products were used to treat patients aged 80 years and upwards, suffering from osteoporosis exhibited by softening of the vertebral body in the lumbar region.

Using an injector device fitted with a trocar, the medicinal product of the invention was injected into the vertebral body to be treated via the posterior and passing through the pedicle.

Approximately 13 g of coral was implanted at a time in each case.

After one month bone reconstruction consolidating the vertebra could be observed (by radiography). The pain due to the vertebral compression attenuated then disappeared.

EXAMPLE 2

Patients aged 80 years and upwards suffering from osteoporosis and suffering from a fracture of the neck of the femur were treated.

Before fitting a metal nail/plate osteosynthesis system, the medicinal product prepared in Example 1 is introduced into the fracture focus so as in each case to implant approximately 20 g of coral.

After one month, radiographic examination demonstrated reconstruction of the bone spans. After three months, a marked increase in the thickness of the cortex of the treated bone was observed. After one year, examination by tomodensitometry showed that the bone mass is 8 times greater than that measured on the opposite, untreated bone.

The patient could return to the standing position earlier than normal.

EXAMPLE 3

Bilateral and symmetrical trephination of the cranium is carried out on rabbits at the level of the parietal bones, by removal of two circular buttons with a diameter of 10 mm.

Five batches of rabbits are taken: four test groups and one control group. A single side is treated in the individuals of each test group.

Group 1 (symbol MF): 50 microliters of methylcellulose gel containing 1 μg of TGF-beta is applied into one of the windows.

Group 2 (symbol BF): 100 μl of biological adhesive to which one 1 μg of TGF-beta was added is applied into one of the windows.

Group 3 (symbol BCF): 50 microliters of a mixture similar to that applied to the BF group, but additionally containing 70 mg of Porites coral granulates marketed under the name BIOCORAL 450 by the Company INOTEB is applied.

Group 4 (symbol BC): the same mixture as for group 3 was applied, but without growth factor.

The evolution of bone construction is followed by cranial tomodensitometry. The diameters and areas of the trephinations are measured on an image analyzer. After sacrifice of the animals studied, after one month, the top of the cranium is sampled then prepared with a microtome for histological analysis by histomorphometry and fluorescence microscopy. In order to label the bone formation surfaces, 2 ml of oxytetraquinol were injected on the tenth and third days preceding sacrifice.

The following observations were made:

After 30 days, groups BC and BCF have completely covered the scar with an osteoid tissue.

For the other groups, covering is not complete. The diameter on the treated side is less than the diameter on the control side. The diameter on the control side is less than the diameters observed in the control group.

The bone span volume (BSV) is determined by histomorphometry.

The BCF group has the highest BSV, followed by the BC group.

Studying the animals in the groups treated with coral shows that the granulates are absorbed progressively. Coral allowed the rapid creation of bone spans between these granulates.

In general, the addition of the growth factor increases the remineralization rate.

We claim:

1. A method of treating a living organism having a disease associated with demineralization or mineralization defects of existing bone, comprising:

applying in a spongy portion of said bone or in a medullary canal of said bone at least one biocompatible and bioabsorbable calcium salt, in the form of particles having dimensions less than 8 mm, said biocompatible and bioabsorbable calcium salt being an active ingredient for reinitiating bone remineralization and reconstruction of resorbed bone spans, and increasing bone density and bone mass of said existing bone.

2. A method according to claim 1, wherein said disease is selected from the group consisting of osteoporosis, Paget's disease, fibrous dysplasias and osteodystrophies.

3. A method according to claim 1, wherein said calcium salt is at least one member selected from the group consisting of gluconate, tartarate, glycerophosphate, sulphate, carbonate and phosphates.

4. A method according to claim 1, wherein said calcium salt is a carbonate.

5. A method according to claim 4, wherein said carbonate is in the form of aragonite or calcite.

6. A method according to claim 5, wherein said carbonate comes from coral skeletons, echinoderm skeletons or mollusc shells.

7. A method according to claim 1, wherein said active ingredient is phosphate-free.

8. A method according to claim 1, wherein said particles have dimensions less than 5 mm.

9. A method according to claim 1, wherein said particles are mixed with at least one substance promoting osteogenesis, allowing said particles to be put into the form of a fluid pastel or both.

10. A method according to claim 9, wherein said substance is at least one member selected from the group consisting of salts of strontium, fluorides, growth factors, blood, blood plasma, bone marrow, collagen, biological adhesives and biocompatible jelling agents.

11. A method according to claim 1, wherein said calcium salt constitutes from 40 to 100% by weight with respect to the total weight of a medicinal product containing said calcium salt.

12. A method according to claim 8, wherein said particles have dimensions ranging from 0.2 to 4 mm.

13. A method according to claim 1, wherein said calcium salt is applied locally by injection or by direct contact application.

14. A method according to claim 1, wherein said remineralization increases the thickness of said bone.

15. A method according to claim 1, wherein said calcium salt is a mixture of different calcium salts which allow the salts to be absorbed into the bone at different rates.

16. A method according to claim 1, wherein said remineralization extends throughout the entire bone from a point of application of said salt.

\* \* \* \* \*